United States Patent [19]

Tsujino et al.

[11] Patent Number: 4,961,925

[45] Date of Patent: Oct. 9, 1990

[54] HAIR PREPARATION COMPOSITION

[75] Inventors: Yoshio Tsujino, Izumisano; Yoshiharu Yokoo, Sagamihara; Kuniaki Sakato, Atsugi; Hiroshi Hagino, Tokyo, all of Japan

[73] Assignee: Kyowa Hakko Kogyo Co., Ltd., Tokyo, Japan

[21] Appl. No.: 283,600

[22] PCT Filed: Mar. 30, 1988

[86] PCT No.: PCT/JP88/00315

§ 371 Date: Nov. 29, 1988

§ 102(e) Date: Nov. 29, 1988

[87] PCT Pub. No.: WO88/07360

PCT Pub. Date: Oct. 6, 1988

[30] Foreign Application Priority Data

Mar. 31, 1987 [JP] Japan ................... 62-78184

[51] Int. Cl.$^5$ .............. A61K 7/09; A61K 7/13; A45D 7/04

[52] U.S. Cl. .................. 424/71; 424/94.4; 424/72; 8/401; 8/406

[58] Field of Search ............ 424/62, 70, 71, 72, 424/94.4; 8/401, 406

[56] References Cited

U.S. PATENT DOCUMENTS 3,251,742  5/1966  Soloway ................... 8/401

FOREIGN PATENT DOCUMENTS 20349  9/1972  Japan ................... 424/94.4
1320250  6/1973  United Kingdom .

Primary Examiner—Merrell C. Cashion, Jr.
Assistant Examiner—Susan S. Rucker
Attorney, Agent, or Firm—Fitzpatrick, Cella, Harper & Scinto

[57] ABSTRACT

The present invention provides a hair preparation composition which contains, as an active ingredient, a dielectron reducing oxidase utilizing oxygen as an acceptor.

8 Claims, No Drawings

HAIR PREPARATION COMPOSITION

TECHNICAL FIELD

The present invention relates to a hair preparation composition characterized in that a dielectron reducing oxidase utilizing oxygen as an acceptor is incorporated as an active ingredient.

BACKGROUND ART

Heretofore, with oxidation hair dyes, for oxidation polymerization of an oxidation dye and in order to bleach hair, hydrogen peroxide, sodium perborate, sodium percarbonate, etc. are used as the oxidizing agent.

Further, in general, for performing a permanent wave, there is employed a method which comprises reducingly cutting the S-S bond in hair with a first solution containing a reducing agent such as thioglycolic acid, cysteine, etc. as a main component and thereafter oxidizingly fixing this hair with a second solution containing an oxidizing agent such as sodium bromate, sodium perborate, hydrogen peroxide etc. as a main component.

However, the use of these oxidizing agents has a disadvantage that they are apt to damage hair and skin.

DISCLOSURE OF THE INVENTION

The present invention is characterized by activating oxygen in air with an oxidase and effectively employing its oxidizing power in the oxidizing course needed for the product.

A first object of the present invention is to provide a hair preparation composition which has a satisfactory effect with a mild oxidizing effect.

A second object of the present invention is to provide a hair preparation composition having an oxidizing function which is low in skin irritation and hardly damages hair and skin, such as an oxidation hair dye, an oxidation agent composition for permanent waving preparation, a bleaching agent for hair or body hair on hands and feet, etc.

The present invention is described in more detail below.

The present invention provides a hair preparation composition which contains at least one dielectron reducing oxidase utilizing oxygen as an acceptor.

The enzyme used in the present invention is a dielectron reducing oxidase utilizing oxygen as an acceptor, and mention is made of, for example, pyranose oxidase (hereinafter referred to as PROD), glucose oxidase (hereinafter referred to as GOD), glycerol oxidase, lactic acid oxidase, pyruvic acid oxidase, uricase, etc.

In the present invention, these enzymes are used either alone or as a combination of two or more thereof.

Further, in order that certain enzymes suitable for the present invention function, cofactors as required. For example, it is known that as cofactors, flavin adenine dinucleotide (hereinafter referred to as FAD) and iron ions are necessary for PROD; FAD and iron ions for GOD; and FAD for pyruvic acid oxidase.

These cofactors are generally contained as impurities in enzymes, and therefore, where the enzyme is described in the present specification, it is understood that it also contains the necessary cofactors unless otherwise specified.

The present invention further provides a hair preparation composition which contains the above-described oxidase and a donor of said enzyme.

The donor varies depending on the enzyme, and for example, there are used D-glucose, L-sorbose and D-xylose for PROD; D-glucose for GOD; glycerol, dihydroxyacetone for glycerol oxidase; lactic acid and its salts for lactic acid oxidase; pyruvic acid and its salts for pyruvic acid oxidase; and uric acid and its salts for uricase.

The amount of the enzyme incorporated is 1 unit/100 g to $1 \times 10^8$ units/100 g, preferably $1 \times 10^2$ units/100 g to $1 \times 10^5$ units/100 g, as the concentration in actual use on hair.

The amount of the donor is 0.01% by weight to 60% by weight, preferably 1% by weight to 35% by weight, as the concentration in actual use on hair.

In the present invention, where D-glucose is used as the donor, PROD is preferred as the enzyme. This is because PROD acts on both α-type and β-type of D-glucose.

Where GOD is used, it is preferred to use it in combination with mutarotase. This is because mutarotase performes rearrangement of D-glucose from α-type to β-type.

It is known that the activity of enzymes can be maintained and stabilized at as high level as possible by the enzyme immobilization method. The immobilized enzyme can be used in the present invention.

In order to solubilize the enzyme also in an organic solvent and further in order that the activity of the enzyme may manifest itself in an organic solvent, it is possible to chemically bind a synthetic polymer or a natural polymer onto the surface of the enzyme protein molecules. This modified enzyme is also included in the enzymes of the present invention.

The present invention also provides a hair dye composition which contains an oxidation hair dye, the above-described enzyme and/or a donor of said enzyme.

The hair dye composition of the present invention is employed in three forms, namely, (1) a hair dye consisting of three packages, (2) a hair dye consisting of two packages, and (3) a hair dye consisting of one package.

As the dye used for the oxidation hair dye, all of the ordinary oxidation dyes may be used. In addition to resorcin, there are described in Hair Dye Standard Material Specifications (third revision, May 1985, Japan Hair Color Industrial Society, Hair Dye Meeting), for example, 5-aminoorthocresol, 3,3′-iminodiphenol, 2,4-diaminophenol hydrochloride, toluene-2,5-diamine hydrochloride, paraphenylenediamine hydrochloride, N-phenylparaphenylenediamine hydrochloride, metaphenylenediamine hydrochloride, orthoaminophenol, catechol, N-phenylparaphenylenediamine acetate, 2,6-diaminopyridine, 1,5-dihydroxynaphthalene, diphenylamine, toluene-2,5-diamine, toluene-3,4-diamine, α-naphthol, paraaminophenylsulfamic acid, paraaminophenol, paraphenylenediamine, paramethylaminophenol, hydroquinone, pyrogallol, N-phenylparaphenylenediamine, phloroglucine, metaaminophenol, metaphenylenediamine, 5-aminoorthocresol sulfate, orthoaminophenol sulfate, orthochloroparaphenylenediamine sulfate, 4,4′-diaminodiphenylamine sulfate, toluene-2,5-diamine sulfate, paraaminophenol sulfate, paraphenylenediamine sulfate, paramethylaminophenol sulfate, metaaminophenol sulfate and metaphenylenediamine sulfate.

Further, 2,4-diaminophenoxyethanol hydrochloride and 5-(2-hydroxyethylamino)-2-methylphenol were also added.

Furthermore, in general, direct dyes often used in combination with oxidation dyes are also included in the oxidation dyes in a wide sense, for example, 2-amino-4-nitrophenol, 2-amino-5-nitrophenol, 1-amino-4-methylaminoanthraquinone, nitroparaphenylenediamine hydrochloride, 1,4-diaminoanthraquinone, nitroparaphenylenediamine, paranitroorthophenylenediamine, picramic acid, sodium picramate, picric acid, 2-amino-5-nitrophenol sulfate, nitroparaphenylenediamine sulfate, paranitroorthophenylenediamine sulfate, paranitrometaphenylenediamine sulfate, etc.

In general, with the oxidation hair dyes, for oxidation polymerization of the oxidation dye and in order to bleach hair, hydrogen peroxide is used at a concentration in use of 1.5% by weight to 4.0% by weight. At this concentration, damage of hair to some degree is inevitable and also skin trouble might be caused depending on the user.

In the present invention, since oxygen in air is activated and utilized, hair damage and skin trouble are less occurred and also the same dyeing and bleaching effects as that by the conventional method may be imparted.

On the other hand, heretofore, there have been found two or three techniques which utilize an enzyme in the hair treating techniques with oxidation hair dyes.

For example, in Japanese Published Unexamined Patent Application No. 10400/1972, there is proposed a method for dyeing hair which comprises (1) a peroxidase enzyme, (2) hydrogen peroxide and (3) an oxidation dye.

Further, in Japanese Published Examined Patent Application No. 47778/1976, there is proposed a composition of dithiothreitol or/and dithioerythritol as a first solution, one, or two or more of the compounds selected from the group (1) tyrosine and/or DL-$\beta$-(3,4-dihydroxyphenyl)alanine or a derivative thereof, (2) 5-hydroxyindole, methyl 5,6-dihydroxyindole-2-carboxylate, tyramine, dopamine, 6-hydroxydopamine and pyrocatechol as a second solution, and a persulfuric acid salt as a third solution, which further incorporates tyrosinase in the second solution or the third solution.

Further, in Japanese Published Examined Patent Application No. 31325/1983, there is also proposed a hair dye consisting of four liquids of (1) pyrocatechol, (2) a watersoluble salt of zinc, copper or iron, (3) a peroxidase and (4) hydrogen peroxide.

These are all those utilizing only the oxidizing effect of the initially incorporated hydrogen peroxide or persulfuric acid salt, and the incorporated hydrogen peroxide or persulfuric acid salt, and the incorporated enzyme is also different, and further, in Japanese Published Examined Patent Application Nos. 47778/1976 and 31325/1983, the precursors of the dyes are specified and thus their intentions are different from the present invention.

Furthermore, the present invention may also be applied to a bleaching agent for unwanted body hair, and a bleaching agent for hair.

In addition, the present invention provides a permanent wave oxidation composition containing a dielectron reducing oxidase utilizing oxygen as an acceptor and a donor of said enzyme, the so-called second solution. Heretofore, the first solution is a reducing agent incorporating thioglycolic acid and/or cysteine, etc., and the second solution is an aqueous solution of an oxidizing agent such as sodium bromate, potassium bromate, sodium perborate, hydrogen peroxide, etc.

In general, the concentration of the hydrogen peroxide is used at 1.0% by weight to 2.5% by weight. At this concentration, damage of hair to some degree is inevitable and skin trouble might be caused depending on the user.

In the present invention, since oxygen in air is utilized, damage of hair and skin trouble are less occurred and also the same oxidation fixing effect as that by the conventional method may be imparted.

Test Examples are given below.

The percent is % by weight, and for the units of the enzyme amounts, there were used D-glucose units for GOD and PROD; uric acid units for uricase; hydrogen peroxide units for peroxidase; and $\alpha$-D-glucose units for mutarotase.

Test Example 1

Dyeing Test

As shown in Table 1, oxidizing solutions were prepared from three kinds of oxidases, i.e. GOD, PROD and uricase and also from combinations of these oxidases with mutarotase and/or peroxidase, and as comparisons, from hydrogen peroxide and purified water alone containing no oxidizing agent.

These were tested for two items. Namely, the hair dyeing effect and the finish of hair were compared and judged according to the following methods and the results are set forth in Table 1.

[Testing Method]

Ten ml of a solution obtained by mixing a dye solution and an oxidizing solution at a ratio of 1:1 is coated on a goat hair bundle of 2 g in weight and 10 cm in length, treated for 30 minutes, washed with water, shampooed and dried.

The evaluation of the dyeing effect and the finish of hair were done according to the following standard.
A: Evaluation of the dyeing effect
  Dyeing properties
  ⊚: Dye in a thick dark brown color
  o: Dyed in a dark brown color
  Δ: Dyed in a shallow dark brown color
  x: Hardly dyed
B: Finish of hair (as compared with the untreated hair)
  o: Soft and combing is smooth
  Δ: Somewhat soft but combing is inferior
  x: Softness is lost and also combing is inferior

TABLE-1

|  | 1-1* | 1-2* | 1-3* | 1-4* | 1-5* | 1-6* |
|---|---|---|---|---|---|---|
| [Dye Solution] | | | | | | |
| Paraphenylenediamine | 0.1% | 0.1% | 0.1% | 0.1% | 0.1% | 0.1% |
| D-Glucose | 3.6 | 3.6 | 3.6 | 3.6 | 3.6 | — |
| Uric acid | — | — | — | — | — | 3.4 |
| Thioglycolic acid | 0.05 | 0.05 | 0.05 | 0.05 | 0.05 | 0.05 |
| Ammonium hydroxide | — | — | — | — | — | — |

TABLE-1-continued

| (30%) Potassium hydroxide | adjusted to pH 7.0 | adjusted to pH 7.0 | adjusted to pH 7.0 | adjusted to pH 7.0 | adjusted to pH 7.0 | adjusted to pH 7.0 |
|---|---|---|---|---|---|---|
| Purified water | | | | Balance | | |
| [Oxidizing Solution] | | | | | | |
| Hydrogen peroxide solution (35%) | — | — | — | — | — | — |
| GOD (2.4 units/mg) | 8.3 | 8.3 | 8.3 | — | — | — |
| PROD (1 unit/mg) | — | — | — | 20.0 | 20.0 | — |
| Uricase (2.8 units/mg) | — | — | — | — | — | 2.0 |
| Mutarotase (0.95 unit/mg) | — | 0.2 | 0.2 | — | — | — |
| Peroxidase (112 units/mg) | — | — | 0.0058 | — | 0.0058 | — |
| Purified water | | | | Balance | | |
| Dyeing Effect | Δ | ○ | ◎ | ○ | ◎ | ◎ |
| Finish of Hair | ○ | ○ | ○ | ○ | ○ | ○ |

| | 1-7* | 1-8* | 1-9* | 1-10* | 1-11 | 1-12 | 1-13 |
|---|---|---|---|---|---|---|---|
| [Dye Solution] | | | | | | | |
| Paraphenylenediamine | 0.1% | 0.1% | 0.1% | 0.1% | 0.1% | 0.1% | 0.1% |
| D-Glucose | — | — | — | — | — | — | — |
| Uric acid | 3.4 | 3.4 | 3.4 | 3.4 | — | — | — |
| Thioglycolic acid | 0.05 | 0.05 | 0.05 | 0.05 | 0.05 | 0.05 | 0.05 |
| Ammonium hydroxide (30%) | — | — | — | — | — | adjusted to pH 10.0 | — |
| Potassium hydroxide | adjusted to pH 8.0 | adjusted to pH 9.0 | adjusted to pH 10.0 | adjusted to pH 7.0 | adjusted to pH 7.0 | — | adjusted to pH 7.0 |
| Purified water | | | | Balance | | | |
| [Oxidizing Solution] | | | | | | | |
| Hydrogen peroxide solution (35%) | — | — | — | — | — | 14.7 | 14.7 |
| GOD (2.4 units/mg) | — | — | — | — | — | — | — |
| PROD (1 unit/mg) | — | — | — | — | — | — | — |
| Uricase (2.8 units/mg) | 2.0 | 2.0 | 2.0 | 2.0 | — | — | — |
| Mutarotase (0.95 unit/mg) | — | — | — | — | — | — | — |
| Peroxidase (112 units/mg) | — | — | — | 0.0058 | — | — | — |
| Purified water | | | | Balance | | | |
| Dyeing Effect | ◎ | ◎ | ◎ | ◎ | x | ◎ | ◎ |
| Finish of Hair | ○ | ○ | ○ | ○ | Δ | x | x |

*Present invention

As seen from the above-described results, the method utilizing hydrogen peroxide as the oxidizing agent is excellent in the dyeing properties, but poor in the finish of hair. By the method utilizing purified water alone, the hair was hardly dyed. According to the present invention, a good finish of hair can be obtained while retaining almost the same dyeing effect as that by using hydrogen peroxide as the oxidizing agent.

Further, the dyeing properties were improved by the combined use with mutarotase and/or peroxidase rather than by using GOD alone.

Test Example 2

Waving Test

After treating with a first solution (reducing agent) of a permanent wave formulation, there was used as a second solution (oxidation agent) a composition incorporating uricase or, as a comparison, a composition incorporating sodium bromate or a composition composed of purified water alone. Three items, i.e. the wave index, wave retention coefficient and degree of skin roughness by an interdigital dropping method were examined by the following methods and the results are set forth in Table 2.

TABLE 2

| [First Solution (Reducing Agent)] | |
|---|---|
| Ammonium thioglycolate (50% as thioglycolic acid) | 13.0% |
| Ammonium hydroxide (30%) | Adjusted to pH 9.0 |
| Purified water | Balance |

| [Second Solution (Oxidation Agent)] | 2-1* | 2-2* | 2-3 | 2-4 |
|---|---|---|---|---|
| Sodium bromate | — | — | — | 8.0% |
| Potassium urate | 2.5% | 2.5% | — | — |
| Uricase (2.8 units/mg) | 2.0 | 2.0 | — | — |
| Peroxidase (112 units/mg) | — | 0.003 | — | — |
| Purified water | | Balance | | |
| Wave index (%) | 61.0 | 59.8 | 60.2 | 59.3 |
| Wave retention coefficient (%) | 58.7 | 62.0 | 4.5 | 62.5 |
| Degree of skin roughness | ○ | ○ | ○ | x |

*Present invention
Note:
The uricase in the formulation is added just before the treatment with the second solution.

[Wave Index and Wave Retention Coefficient Measuring Tests]

(I) Twenty hairs described below were made into a bundle, fixed to a plastic measuring comb by winding the hairs in zigzags, dipped in the first solution (reducing agent) having the composition shown in Table 2 at 30° C. for 10 minutes, then rinsed thoroughly with water, and thereafter dipped in the second solution (oxidation agent) at 30° C. for 10 minutes respectively. After rinsing with water, it was removed from the measuring comb, and the degree of waving was measured according to Kirby method (Proceedings of the Scientific Section, Vol. 26, p. 12, 1956).

Hair: Human hair of 15 cm in length (10-year-old female, untreated hair), washed with a 10% aqueous solution of sodium laurylsulfate and dried in air.

(II) The hair used in (I) was dipped in a 10% aqueous solution of sodium laurylsulfate at 60° C. for 20 minutes, washed with water and maltreated. Its wave index was compared with the wave index before the maltreatment and the wave retention coefficient was calculated according to the following equation.

$$100 - \frac{(\text{Wave Index} - \text{Wave Index before Maltreatment})}{\text{Wave Index}} \times 100$$

[Test by an Interdigital Dropping Method]

Three parts between fingers (between the second and third fingers, between the third and fourth fingers and between the fourth and fifth fingers) of either of right and left hand of the panel were examined to confirm that there is no abnormality of the skin. Thereafter, the second solution (oxidation agent) of the composition shown in Table 2 was dropped on the interdigital parts at a rate of 0.7 ml/min by a constant flow rate pump for 10 minutes, left for 5 minutes, washed with warm water of about 40° C. for 15 seconds, and dried with towel; this operation was repeated twice a day for 6 days, between the former three days and the latter three days, a two-day interval was taken, and the degree of skin roughness was observed by comparing with the hand not tested.

The experimental panel was consisted of 20 females of 22–52 years old. The evaluation of the degree of skin roughness was done according to the following standard.

A: Evaluation of Skin Roughness
 o: Skin roughness is not observed.
 Δ: Minute wrinkles are observed.
 x: Wrinkles, dryness and roughness of skin are observed.

From the above-described results, it is obvious that the present invention has the same waving effect as the conventional product incorporating sodium bromate and that there is almost no waving effect with purified water alone.

Further, with the product incorporating sodium bromate, skin roughness is observed, while with the oxidation agent of the present invention, the skin roughness of the panel is remarkably prevented.

EXAMPLES

The present invention is described in more detail by the following examples.

EXAMPLE 1

One-package Hair Dye (Cream)

| | |
|---|---|
| Paraphenylenediamine | 1.35% |
| Orthoaminophenol | 0.1 |
| Resorcin | 0.25 |
| Cetanol | 6.0 |
| Oleyl alcohol | 5.0 |
| Polyoxyethylene cetyl ether (15 E.O.) | 7.0 |
| Liquid paraffin | 10.0 |
| Stearyltrimethylammonium chloride | 1.0 |
| Propylene glycol | 2.0 |
| Uricase (2.8 units/mg) | 1.0 |
| Uric acid | 5.3 |
| Disodium edetate | 0.2 |
| Thioglycolic acid | 0.1 |
| Monoethanolamine, purified water | Balance |

(The pH is adjusted to 8.5 with monoethanolamine.)

This composition is coated on a white hair, which is treated at 30° C. for 30 minutes, then washed with water, shampooed and dried.

The white hair was dyed in grayish color.

EXAMPLE 2

One-package Hair Dye (Gel)

| | |
|---|---|
| Paraphenylenediamine | 0.08% |
| Orthoaminophenol | 0.04 |
| Nitroparaphenylenediamine | 0.4 |
| 2-Amino-4-nitrophenol | 0.4 |
| Resorcin | 0.1 |
| Sodium carboxymethyl cellolose | 7.5 |
| Uricase (2.8 units/mg) | 1.07 |
| Potassium urate | 2.44 |
| Thioglycolic acid | 0.1 |
| Purified water | Balance |

This composition is coated on a white hair, which is treated at 30° C. for 30 minutes, then washed with water, shampooed and dried.

The white hair was dyed in reddish brown color.

EXAMPLE 3

One-package Hair Dye (Hair cream type)

| | |
|---|---|
| Paraphenylenediamine | 0.135% |
| Orthoaminophenol | 0.01 |
| Resorcin | 0.025 |
| Cetanol | 6.0 |
| Oleyl alcohol | 5.0 |
| Polyoxyethylene cetyl ether (15 E.O.) | 7.0 |
| Polyoxyethylene cetyl ether (10 E.O.) | 3.5 |
| Liquid paraffin | 10.0 |
| Stearyltrimethylammonium chloride | 1.0 |
| Liquid lanolin | 1.0 |
| Uricase (2.8 units/mg) | 1.0 |
| Uric acid | 1.1% |
| Disodium edetate | 0.2 |
| Ascorbic acid | 0.2 |
| Potassium hydroxide, purified water | Balance |

(The pH is adjusted to 7.5 with potassium hydroxide.)

This composition is coated on a white hair, which is treated for 10 to 30 minutes. The hair is immediately washed or shampooed and dried.

This composition was similarly used on the white hair every day for 10 days, to find that the hair had been dyed in grayish color.

EXAMPLE 4

One-package Hair Dye (Treatment type)

| | |
|---|---|
| Paraphenylenediamine | 0.04% |
| Orthoaminophenol | 0.02 |
| Nitroparaphenylenediamine | 0.20 |
| 2-Amino-4-nitrophenol | 0.20 |
| Resorcin | 0.05 |
| Cetyltrimethylammonium chloride | 2.5 |
| Stearyltrimethylammonium chloride | 1.0 |
| Isopropyl myristylate | 7.0 |
| Cetanol | 5.0 |
| Stearyl alcohol | 2.0 |

| | |
|---|---|
| Liquid paraffin | 4.0 |
| Liquid lanolin | 0.5 |
| Propylene glycol | 0.5 |
| Uricase (2.8 units/mg) | 1.0 |
| Uric acid | 5.1 |
| Peroxidase (112 units/mg) | 0.003 |
| Thioglycolic acid | 0.1 |
| Potassium hydroxide, purified water | Balance |

(The pH is adjusted to 7.5 with potassium hydroxide.)

This composition is coated on a white hair, which is treated at 30° C. for 30 minutes, then washed with water, shampooed and dried. The white hair was dyed in reddish brown color. Further, like the conventional hair treatment, it was coated on the previously shampooed hair, which was treated at 30° to 40° C. for 5 to 10 minutes, and washed with water.

This precedure was repeated on the white hair for 10 days, to find that the hair was dyed in reddish brown color.

EXAMPLE 5

One-package Hair Dye (Powder)

| | |
|---|---|
| Paraphenylenediamine sulfate | 10.0% |
| Orthoaminophenol sulfate | 3.0 |
| Paramethylaminophenol sulfate | 2.0 |
| Sodium carboxymethyl cellulose | 24.0 |
| Sodium carbonate | 7.36 |
| Uric acid | 14.17 |
| Uricase (2.8 units/mg) | 8.30 |
| Dextrin | Balance |

First, to 6 g of the above-described composition is added purified water until the total volume is 50 ml, for preparation of a dye solution.

This dye solution is coated on a white hair, which is treated at 30° C. for 30 minutes, washed with water, shampooed and dried.

The white hair was dyed in dark reddish brown color.

In this powder hair dye, where water is not contained in the starting material, the stability was improved.

EXAMPLE 6

Aerosol Type Hair Dye

[Stock Solution]

| [Stock Solution] | |
|---|---|
| Paraphenylenediamine | 0.4% |
| Paraaminophenol | 0.1 |
| Orthoaminophenol | 0.5 |
| Resorcin | 0.8 |
| PROD (1 unit/mg) | 10.0 |
| D-Glucose | 5.5 |
| Propylene glycol | 2.0 |
| Thioglycolic acid | 0.1% |
| 0.1 M Phosphate buffer (pH 6.5) | Balance |

First, the above-described composition is injected into a piston can (double container system, FIG. 1), and then carbon dioxide is injected from a gas filling line so that the initial volume be about ⅓ of the container and the initial pressure be about 8 to 9 kg/cm² to prepare an aerosol type hair dye.

As the propellant, there may be used a compressed gas such as nitrogen and laughing gas as well as carbon dioxide and a liquefied gas such as Furon 11, 12, 114 and LPG either alone or in combination.

This hair dye is coated on a white hair, which is treated at 30° C. for 30 minutes, washed with water, shampooed and dried.

The white hair was dyed in grayish color.

This aerosol type hair dye has improved stability of PROD since it is brought into contact with air and/or the propellant during storage. Further, it is also possible to replace the piston can by a bag-in can and an EXXEL SYSTEM (product of CONTAINER INDUSTRIES INC., America) which ejects the contents by directly applying the rubber pressure to the container.

EXAMPLE 7

Two-packages Hair Dye (Shampoo Type)

| | |
|---|---|
| Paraphenylenediamine | 0.28% |
| Paraaminophenol | 0.1 |
| Orthoaminophenol | 0.14 |
| Nitroparaphenylenediamine | 0.02 |
| Resorcin | 0.4 |
| Polyoxyethylene lauryl ether sodium sulfate (3 E.O.) | 10.0 |
| Coconut oil fatty acid amide propyldimethylaminoacetic acid betaine | 4.0 |
| Coconut oil fatty acid diethanolamide | 5.0 |
| D-Glucose | 5.5% |
| Propylene glycol | 1.0 |
| GOD (2.4 units/mg) | 4.15 |
| Mutarotase (0.95 units/mg) | 0.1 |
| Peroxidase (112 units/mg) | 0.0029 |
| 0.1 M phosphate buffer (pH 6.5) | Balance |

Note:
GOD and mutarotase in this formulation are added just before the hair dyeing treatment.

This composition is coated on a white hair, which is treated at 30° C. for 30 minutes, washed with water and dried.

The white hair was dyed in slightly purple-tinted brown color.

Further, like the conventional shampoo, this composition is coated on a white hair at 30° C. for 3 to 5 minutes, then immediately washed with water and dried. When this procedure was repeated on the white hair once a day for 10 days, it was dyed in slightly purple-tinted brown color.

EXAMPLE 8

Two-packages Hair Dye

[Coloring Base]

| | |
|---|---|
| Paraphenylenediamine | 2.7% |
| Orthoaminophenol | 0.2 |
| Resorcin | 0.5 |
| Sodium laurylsulfate | 1.0 |
| D-Glucose | 11.0 |
| Disodium editate | 0.1 |
| Ascorbic acid | 0.4 |
| Ammonium hydroxide, Purified water | Balance |

(The pH is adjusted to 7.0 with ammonium hydroxide.)

[Enzyme solution]

| | |
|---|---|
| PROD (1 unit/mg) | 20.0% |
| Peroxidase (112 units/mg) | 0.006 |
| Glycerin | 3.0 |

| | |
|---|---|
| 0.1 M Phosphate buffer (pH 6.5) | Balance |

First, a solution obtained by mixing the coloring base and the enzyme solution at a ratio of 1:1 is coated on a white hair, which is treated at 30° C. for 30 minutes, then washed with water, shampooed and dried.

The white hair was dyed in grayish color.

EXAMPLE 9

Two-packages Hair Dye

[Coloring Base]

| | |
|---|---|
| Paraphenylenediamine | 0.8% |
| Paraaminophenol | 0.2 |
| Orthoaminophenol | 1.0 |
| Resorcin | 1.6 |
| Oleic acid | 20.0 |
| Bis-2-Hydroxyethylsorbitanamine | 9.0 |
| Hydroxyethylstearylamide | 6.0 |
| Propylene glycol | 12.0 |
| Isopropanol | 10.0 |
| Disodium edetate | 0.3 |
| Sodium sulfite | 0.3 |
| Ammonium hydroxide, purified water | Balance |

(The pH is adjusted to 8.5 with ammonium hydroxide.)

[Enxyme Powder]

| | |
|---|---|
| Uricase (2.8 units/mg) | 15.4% |
| Uric acid | 84.6 |

First, a solution obtained by mixing the coloring base and the enzyme powder at a ratio of 14:1 is coated on a white hair, which is treated at 30° C. for 30 minutes, washed with water, shampooed, and dried.

The white hair was dyed in gray-tinted brown color.

EXAMPLE 10

Three-packages Hair Dye

[Coloring Base]

| | |
|---|---|
| Paraphenylenediamine | 0.56% |
| Paraaminophenol | 0.20 |
| Orthoaminophenol | 0.28 |
| Nitroparaphenylenediamine | 0.04 |
| Resorcin | 0.80% |
| Liquid paraffin | 5.0 |
| Lanolin alcohol | 2.0 |
| Polyoxyethylene lauryl ether phosphate (3 E.O.) | 2.0 |
| Lauric acid diethanolamide | 5.0 |
| Thioglycolic acid | 0.2 |
| Disodium edetate | 0.1 |
| 0.1 M Phosphate buffer (pH 6.5) | Balance |

[Substrate Solution]

| | |
|---|---|
| D-Glucose | 21.6% |
| Purified water | Balance |

[Enzyme Solution]

| | |
|---|---|
| Mutarotase (0.95 unit/mg) | 0.4% |
| GOD (2.4 units/mg) | 16.6 |
| Peroxidase (112 units/mg) | 0.0116 |
| Glycerin | 3.0 |
| 0.1 M Phosphate buffer (pH 7.0) | Balance |

First, a solution obtained by mixing the coloring base, the substrate solution and the enzyme solution at a ratio of 2:1:1 is coated on a white hair, which is treated at 30° C. for 30 minutes, washed with water, shampooed and dried.

The white hair was dyed in slightly purple-tinted brown color.

EXAMPLE 11

Cold Waving Preparation Mainly Containing Thioglycolic Acid (Thioglycolic Acid-based Permanent Waving Agent)

[First Solution (Reducing Agent)]

| | |
|---|---|
| Ammonium thioglycolate solution (50% as thioglycolic acid) | 13.0% |
| Polyoxyethylene oleyl ether (10 E.O.) | 1.0 |
| Polyoxyethylene oleyl ether (20 E.O.) | 1.0 |
| Sodium lauryl sulfate | 0.5 |
| Hydrolyzed collagen solution (20%) | 2.0 |
| Disodium edetate | 0.1% |
| Ammonium hydroxide, purified water | Balance |

(The pH is adjusted to 9.1 with ammonium hydroxide.)

[Second Solution (Oxidation Agent)]

| | |
|---|---|
| PROD (1 unit/mg) | 20.0% |
| Peroxidase (112 units/mg) | 0.0058 |
| D-Glucose | 3.6 |
| Glycerin | 3.0 |
| Purified water | Balance |

Note: PROD in the formulation is added just before the treatment with the second solution.

First, in a conventional manner, a hair is protected on the tip with paper, wound on a plastic rod of 1.5 cm in diameter, dipped in the first solution of the above-described composition at 30° C. for 10 minutes, washed with running water for 1 minute, then dipped in the second solution at 30° C. for 10 minutes, and washed with water, to thereby conduct permanent waving treatment.

As a result, the hair was imparted with a uniform wave from the root to the tip, and also the touch was good.

EXAMPLE 12

Cold Waving Preparation Mainly Containing Cysteine (Cysteine-based Permanent Waving Agent)

[First Solution (Reducing Agent)]

| | |
|---|---|
| L-Cysteine Hydrochloride | 7.0% |
| Cetanol | 0.5 |
| Oleyl alcohol | 0.5 |
| Polyoxyethylene cetyl ether (10 E.O.) | 1.0 |
| Polyoxyethylene cetyl ether (15 E.O.) | 1.0 |
| Disodium edetate | 0.1 |

-continued

| Monoethanolamine, purified water | Balance |
|---|---|

(The pH is adjusted to 9.1 with monoethanolamine.)

[Second Solution (Oxidation Agent)]

| GOD (2.4 units/mg) | 8.3% |
|---|---|
| Mutarotase (0.95 unit/mg) | 0.2% |
| Peroxidase (112 units/mg) | 0.0058 |
| D-Glucose | 3.6 |
| Sorbitol | 3.0 |
| Purified water | Balance |

Note:
GOD in the formulation is added just before the treatment with the second solution.

Using the above-described composition, permanent waving treatment was conducted in a manner similar to that in Example 11.

As a result, the hair was imparted with a uniform wave from the root to the tip, and also the touch was good.

EXAMPLE 13

Heat-Waving Preparation Mainly Containing Thioglycolic Acid

[First Solution (Reducing Agent)]

| Ammonium thioglycolate (50% as thioglycolic acid) | 10.0% |
|---|---|
| Cetanol | 0.5 |
| Oleyl alchol | 0.5 |
| Polyoxyethyl cetyl ether (10 E.O.) | 0.5 |
| Polyocyethyl cetyl ether (15 E.O.) | 1.0 |
| Disodium editate | 0.1 |
| Ammonium bicarbonate, purified water | Balance |

(The pH is adjusted to 7.5 with ammonium bicarbonate.)

[Second Solution (Oxidation Agent)]

The same agent as the second solution in Example 11 is used.

Using the above-described composition, permanent waving treatment was conducted in a manner similar to that in Example 10, except that both treatments with the first solution and the second solution were conducted at 45° C.

As a result, the hair was imparted with a uniform wave from the root to the tip, and also the touch was good.

We claim:

1. A hair dye composition which comprises a dielectron reducing oxidase utilizing oxygen as an acceptor, a donor of said oxidase, an oxidation dye which is oxidizable by hydrogen peroxide to develop color, water and a cosmetically acceptable vehicle.

2. The hair dye composition according to claim 1, wherein the dielectron reducing oxidase is at least one member selected from the group consisting of pyranose oxidase, glucose oxidase, glycerol oxidase, lactic acid oxidase, pyruvic acid oxidase and uricase.

3. An oxidation composition for permanent waving preparation, which comprises a dielectron reducing oxidase utilizing oxygen as an acceptor, a donor of said oxidase, water and a cosmetically acceptable vehicle.

4. The oxidation composition for permanent waving preparation according to claim 7, wherein the dielectron reducing oxidase is at least one member selected from the group consisting of pyranose oxidase, glucose oxidase, glycerol oxidase, lactic acid oxidase, pyruvic acid oxidase and uricase.

5. A hair preparation composition which comprises a dielectron reducing oxidase utilizing oxygen as an acceptor, a donor of said oxidase, water, a peroxidase and a cosmetically acceptable vehicle.

6. A hair preparation composition, which comprises glucose oxidase, mutarotase, a donor of glucose oxidase, water and a cosmetically acceptable vehicle.

7. A method for dyeing hair, which comprises:
 (i) subjecting a donor of a dielectron reducing oxidase utilizing oxygen as an acceptor on hair to air oxidation in the presence of said oxidase and water to thereby form hydrogen peroxide,
 (ii) oxidizing an oxidation dye by hydrogen peroxide to develop color on hair, and
 (iii) washing colored hair with water.

8. The method according to claim 7, wherein the dielectron reducing oxidase is at least one member selected from the group consisting of pyranose oxidase, glucose oxidase, glycerol oxidase, lactic acid oxidase, pyruvic acid oxidase and uricase.

* * * * *

UNITED STATES PATENT AND TRADEMARK OFFICE
CERTIFICATE OF CORRECTION

PATENT NO. : 4,961,925

DATED : October 9, 1990

INVENTOR(S) : YOSHIO TSUJINO

It is certified that error appears in the above-identified patent and that said Letters Patent is hereby corrected as shown below:

Column 14, line 22, "claim 7," should read --claim 3,--.

Signed and Sealed this

Twenty-eighth Day of January, 1992

Attest:

HARRY F. MANBECK, JR.

*Attesting Officer*      *Commissioner of Patents and Trademarks*

UNITED STATES PATENT AND TRADEMARK OFFICE
CERTIFICATE OF CORRECTION

PATENT NO. : 4,961,925
DATED : 10/9/90
INVENTOR(S) : YOSHIO TSUJINO, ET AL.

It is certified that error appears in the above-identified patent and that said Letters Patent is hereby corrected as shown below:

>   Title Page, at [73] Assignee:, after "Tokyo, Japan", add --and YAMAHATSU SANGYO CO., LTD., Osaka, Japan--.

Signed and Sealed this

Twenty-first Day of April, 1992

Attest:

HARRY F. MANBECK, JR.

*Attesting Officer*     *Commissioner of Patents and Trademarks*